United States Patent
Hu et al.

(10) Patent No.: US 10,920,568 B2
(45) Date of Patent: Feb. 16, 2021

(54) EVALUATING CEMENT INTEGRITY IN A WELLBORE WITH MULTIPLE CASING STRINGS

(71) Applicant: Halliburton Energy Services, Inc., Houston, TX (US)

(72) Inventors: Yike Hu, Houston, TX (US); Weijun Guo, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/751,301

(22) PCT Filed: Mar. 10, 2017

(86) PCT No.: PCT/US2017/021839
§ 371 (c)(1),
(2) Date: Feb. 8, 2018

(87) PCT Pub. No.: WO2018/164694
PCT Pub. Date: Sep. 13, 2018

(65) Prior Publication Data
US 2020/0199995 A1    Jun. 25, 2020

(51) Int. Cl.
G01N 33/38 (2006.01)
E21B 47/00 (2012.01)
E21B 47/005 (2012.01)

(52) U.S. Cl.
CPC ......... *E21B 47/005* (2020.05); *G01N 33/383* (2013.01)

(58) Field of Classification Search
CPC .......................... E21B 47/005; G01N 33/383
See application file for complete search history.

(56) References Cited

U.S. PATENT DOCUMENTS

| 6,041,861 A | 3/2000 | Mandal et al. |
| 8,963,072 B2 | 2/2015 | Luling |

(Continued)

FOREIGN PATENT DOCUMENTS

| WO | WO 2016/053344 A1 | 4/2016 |
| WO | WO 2016/187239 A1 | 11/2016 |
| WO | WO 2017/008078 A2 | 1/2017 |

OTHER PUBLICATIONS

Blount et al., "A Cement Channel-Detection Technique Using the Pulsed-Neutron Log," Society of Petroleum Engineers Formation Evaluation vol. 6, Issue 4, Dec. 1991, pp. 485-492.

(Continued)

*Primary Examiner* — Mark R Gaworecki
(74) *Attorney, Agent, or Firm* — Haynes and Boone, LLP

(57) ABSTRACT

A system and method for evaluating integrity of cement in a wellbore with multiple casing strings. The system and method may include at least one source that can emit a field of photons, and at least one photon detector spaced away from the source by a first distance that configures the tool to measure cement integrity in a first annulus, by a portion of the source photons being scattered back to the first detector which can produce photon count rates based on energy levels of received photons. Integrity of cement in the first annulus can be determined by the photon count rates. A second detector spaced a second distance from the source can be included and can measure cement integrity in a second annulus that is radially outside the first annulus by producing photon count rates for photons received from the second annulus.

23 Claims, 9 Drawing Sheets

(56) References Cited

U.S. PATENT DOCUMENTS

| | | |
|---|---|---|
| 9,057,795 B2 | 6/2015 | Guo et al. |
| 2015/0219780 A1 | 8/2015 | Zeroug et al. |
| 2016/0282505 A1* | 9/2016 | Lee .................. G01V 5/125 |
| 2016/0291198 A1* | 10/2016 | Lee .................. G01V 5/125 |
| 2017/0199298 A1* | 7/2017 | Hu .................. E21B 47/005 |

OTHER PUBLICATIONS

International Search Report and the Written Opinion of the International Search Authority, or the Declaration, Dec. 8, 2017, PCT/US2017/021839, 18 pages, ISA/KR.

Moake et al., "Design of a Cased-Hole-Density Logging Tool Using Laboratory Measurements," Society of Petroleum Engineers Annual Technical Conference and Exhibition, Sep. 27-30, 1998, New Orleans, Louisiana, USA.

Soilee, "Gravel-Pack Logging Experiments," Society of Petroleum Engineers 60 Annual Technical Conference and Exhibition, Sep. 22-25, 1985, Las Vegas, Nevada, USA.

Zaini et al., "Improved Casing Integrity Evaluation Enable Multiple Strings Metal-Loss Profilling in Aging Wells," Offshore Technology Conference, Mar. 22-25, 2016, Kuala Lumpur, Malaysia.

\* cited by examiner

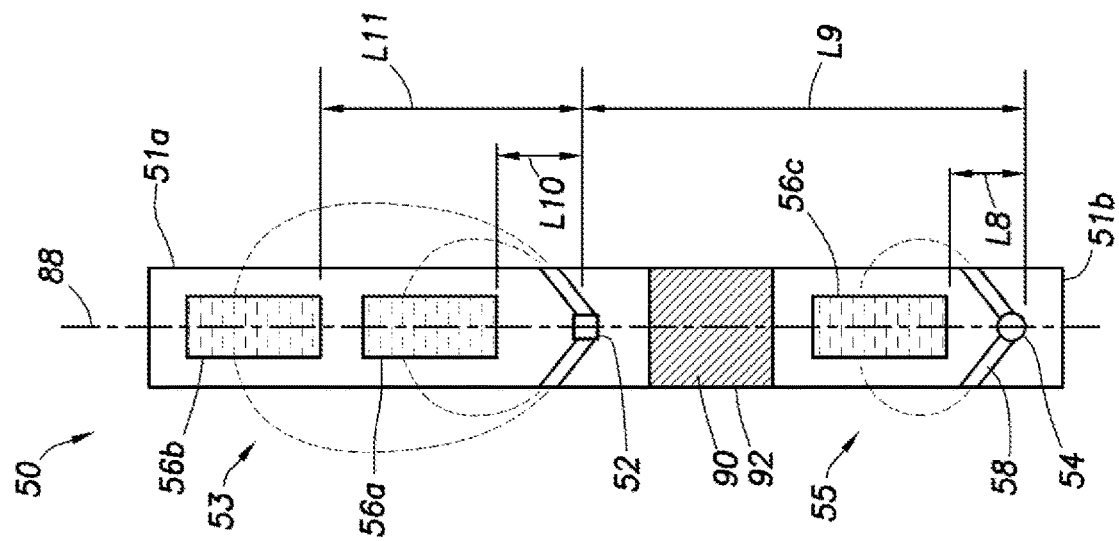
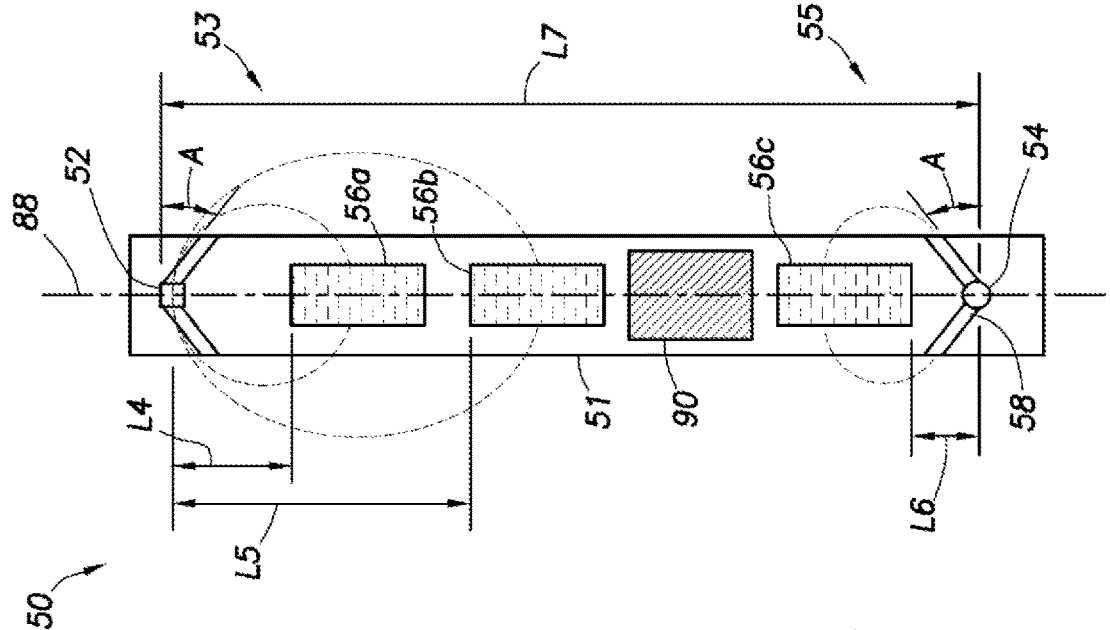
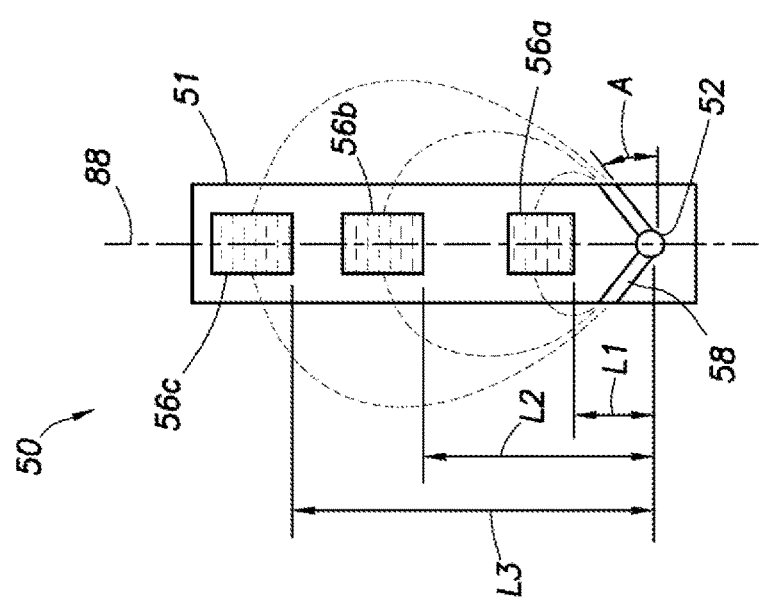
FIG. 4C
FIG. 4B
FIG. 4A

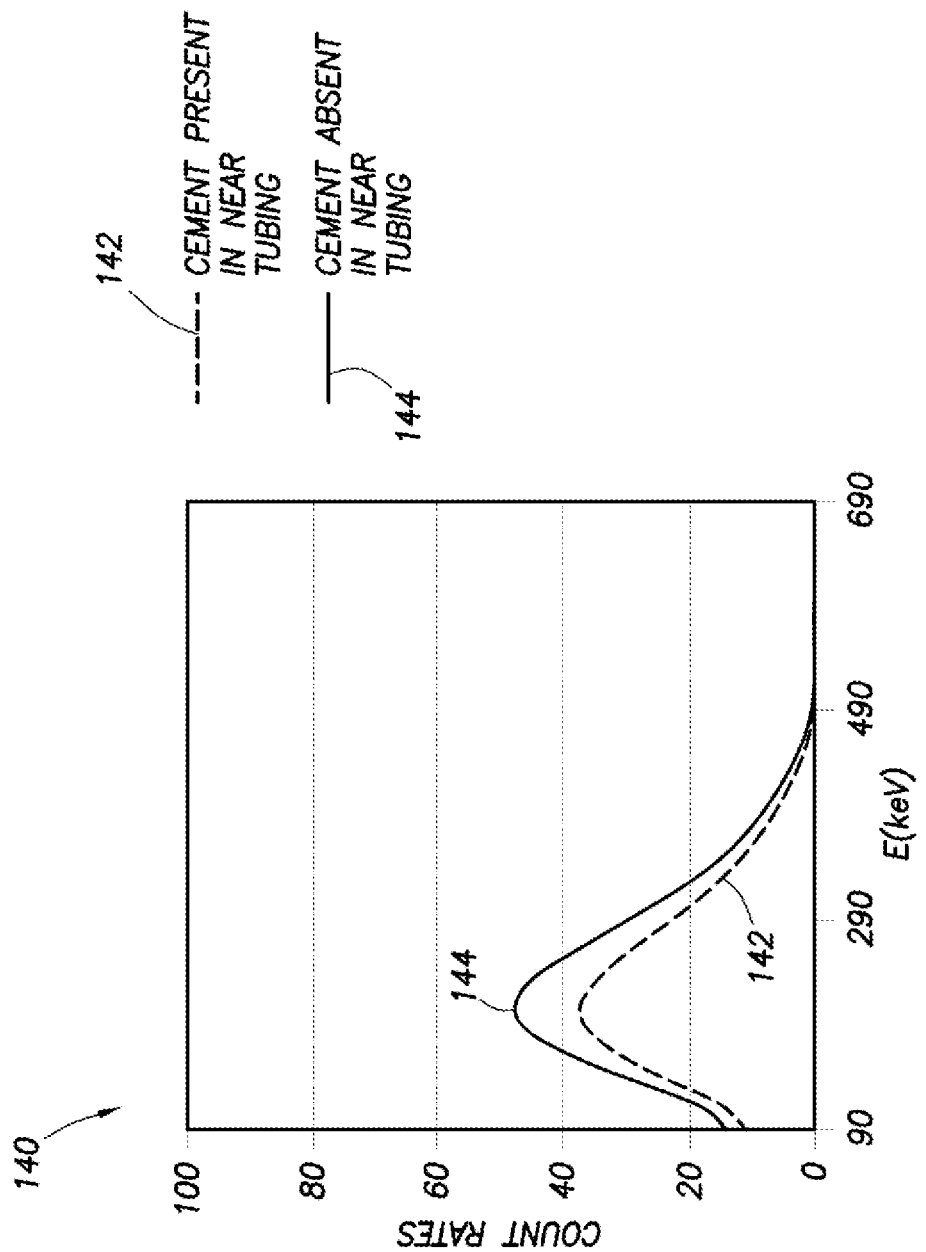

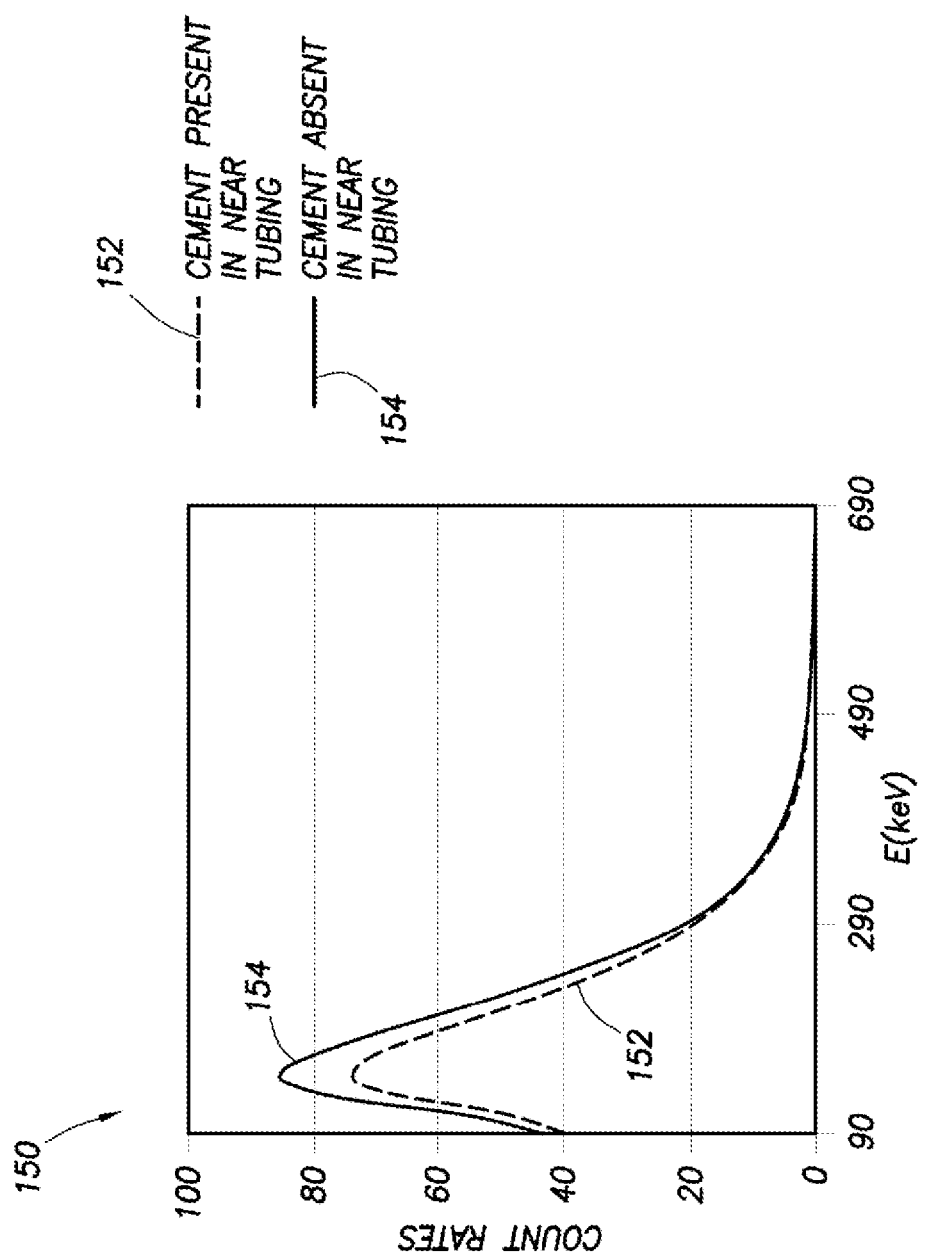

EVALUATING CEMENT INTEGRITY IN A WELLBORE WITH MULTIPLE CASING STRINGS

CROSS-REFERENCE TO RELATED APPLICATION

The present application is a U.S. National Stage patent application of International Patent Application No. PCT/US2017/021839, filed on Mar. 10, 2017, the benefit of which is claimed and the disclosure of which is incorporated herein by reference in its entirety.

TECHNICAL FIELD

The present disclosure generally relates to oilfield equipment and, in particular, to downhole tools, drilling and related systems and techniques for evaluating integrity of cement in a multi-string configuration. More particularly still, the present disclosure relates to methods and systems for evaluating integrity of cement in a multi-string configuration by measuring count rates of photons (or gamma rays) scattered back to the wellbore by material(s) surrounding the wellbore, and calculating the cement integrity based on the counts rates.

BACKGROUND

A gamma ray scintillation type detector consists of a scintillation crystal optically coupled to a photomultiplier tube. Intensity of light induced within the crystal by an impinging gamma ray is proportional to the energy of the gamma ray. The optically coupled photomultiplier tube generates an electrical pulse which is proportional to the intensity of the light generated within the scintillation crystal. It follows, therefore, that the electrical pulse generated by the photomultiplier tube is proportional to the energy of the gamma ray impinging upon the scintillation crystal. These electrical pulses can be counted based on their energy level, which follows that such counts can be seen as a count rate of gamma rays at a particular energy level that have been detected by the scintillation crystal (or any other suitable gamma ray or photon detector). These counts can be grouped together to represent one or more count rates for particular energy ranges (or energy windows) of the collected gamma rays (or photons) or combined to represent an overall count rate for all energy ranges.

These count rates can be used to determine characteristics of material(s), such as cement, surrounding the wellbore during logging operations. Logging wellbore characteristics during or after a wellbore is formed can provide valuable information about the material(s) surrounding the wellbore, such as cement integrity, presence and/or absence of cement, etc. Current methods for determining integrity of the cement that may be used to hold casing strings in place may have issues when multiple casing strings are installed in the wellbore.

Therefore, it will be readily appreciated that improvements in the arts of using gamma ray count rates to determine cement integrity in multiple cased wellbores are continually needed.

BRIEF DESCRIPTION OF THE DRAWINGS

Various embodiments of the present disclosure will be understood more fully from the detailed description given below and from the accompanying drawings of various embodiments of the disclosure. In the drawings, like reference numbers may indicate identical or functionally similar elements. Embodiments are described in detail hereinafter with reference to the accompanying figures, in which:

FIGS. 4A-4C are representative block diagrams of example configurations of the logging tool;

FIG. 9 is a representative plot of photon count rates vs. energy levels of collected photons for two conditions, one with cement present and one with cement absent;

FIG. 10 is another representative plot of photon count rates vs. energy levels of collected photons for two conditions, one with cement present and one with cement absent;

DETAILED DESCRIPTION OF THE DISCLOSURE

Figure 1:
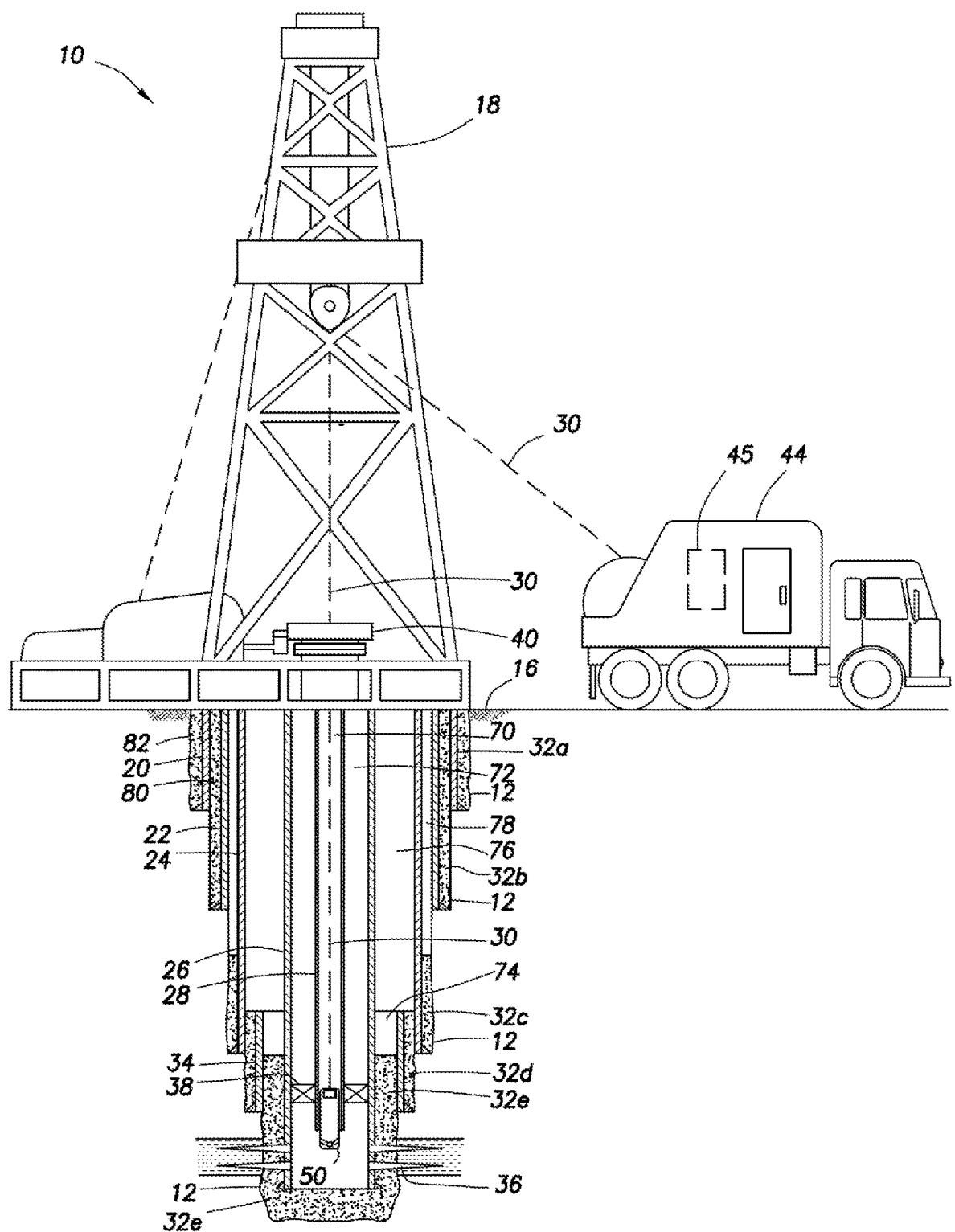
FIG. 1 is a representative partial cross-sectional view of a system for capturing subsurface measurement data in a wireline logging operation in a wellbore with multiple casing strings, according to one or more example embodiments.

The disclosure may repeat reference numerals and/or letters in the various examples or Figures. This repetition is for the purpose of simplicity and clarity and does not in itself dictate a relationship between the various embodiments and/or configurations discussed. Further, spatially relative terms, such as beneath, below, lower, above, upper, uphole, downhole, upstream, downstream, and the like, may be used herein for ease of description to describe one element or feature's relationship to another element(s) or feature(s) as illustrated, the upward direction being toward the top of the corresponding figure and the downward direction being toward the bottom of the corresponding figure, the uphole direction being toward the surface of the wellbore, the downhole direction being toward the toe of the wellbore. Unless otherwise stated, the spatially relative terms are intended to encompass different orientations of the apparatus in use or operation in addition to the orientation depicted in the Figures. For example, if an apparatus in the Figures is turned over, elements described as being "below" or "beneath" other elements or features would then be oriented "above" the other elements or features. Thus, the exemplary term "below" can encompass both an orientation of above and below. The apparatus may be otherwise oriented (rotated 90 degrees or at other orientations) and the spatially relative descriptors used herein may likewise be interpreted accordingly.

Moreover even though a Figure may depict a horizontal wellbore or a vertical wellbore, unless indicated otherwise, it should be understood by those skilled in the art that the apparatus according to the present disclosure is equally well suited for use in wellbores having other orientations including vertical wellbores, slanted wellbores, multilateral wellbores or the like. Likewise, unless otherwise noted, even though a Figure may depict an offshore operation, it should be understood by those skilled in the art that the method and/or system according to the present disclosure is equally well suited for use in onshore operations and vice-versa. Further, unless otherwise noted, even though a Figure may depict a cased hole, it should be understood by those skilled in the art that the method and/or system according to the present disclosure is equally well suited for use in open hole operations.

As used herein, the words "comprise," "have," "include," and all grammatical variations thereof are each intended to have an open, non-limiting meaning that does not exclude additional elements or steps. While compositions and methods are described in terms of "comprising," "containing," or "including" various components or steps, the compositions and methods also can "consist essentially of" or "consist of" the various components and steps. It should also be understood that, as used herein, "first," "second," and "third," are assigned arbitrarily and are merely intended to differentiate between two or more objects, etc., as the case may be, and does not indicate any sequence. Furthermore, it is to be understood that the mere use of the word "first" does not require that there be any "second," and the mere use of the word "second" does not require that there be any "first" or "third," etc.

The terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

Generally, this disclosure provides a system and method for evaluating an integrity of cement in a wellbore with multiple casing strings. The system and method may include a tool with one or more detector/source sets contained in a body. A first set can include a first collimated photon source that produces a field of photons emitted from the first source (e.g. a substantially cone-shaped field, a panoramic field, etc.), and one or more non-azimuthally collimated photon detectors spaced with each spaced away from the first photon source by a longitudinal distance. The distance between each source and detector can configure the tool (along with the energy level of the source) such that the first source photons travels to one or more annuli positioned radially outside a one or more casing strings, with at least a portion of the first source photons that travel into the annuli are scattered back to the one or more detectors.

A first detector can be configured to receive the scattered photons from the first annulus and produce photon count rates produced based on energy levels of the first source scattered photons that are received by the first detector. A presence or absence of cement in the first annulus can be determined by the first detector count rates, by comparing these first detector count rates with expected count rates for the first annulus. The expected count rates can be determined by prior collected data, computer simulation of the wellbore 12, etc. The first detector can be configured to simultaneously receive scattered photons from the first annulus at substantially any azimuthal direction around a circumference of the first detector. The other detectors can be configured to receive the scattered photons from various annuli and produce count rates based on energy levels of the received photons. These count rates can be used to determine, the presence of cement in these annuli as well as an integrity of the cement in these annuli.

FIG. 1 shows an elevation view in partial cross-section of a wellbore system 10 which can be utilized for wireline and slickline operations in a wellbore 12. Wellbore 12 can extend through various earth strata in an oil and gas formation 14 located below the earth's surface 16. Wellbore system 10 can include a rig (or derrick) 18 and a wellhead 40. A conveyance 30 (such as wireline, slickline, coiled tubing, etc.), can be used to raise and lower a logging tool 50 into and out of the wellbore 12. The logging tool 50 can be used to evaluate the integrity of cement in a wellbore 12 with multiple casing strings 20, 22, 24, 26, 34. As used herein, "cement" refers to a slurry that is deposited in an annulus between a tubing string (such as casing) and a wellbore wall and hardens to a solid material that seals the portion of the annulus filled by the hardened cement. So "cement" refers to both the slurry and the material that results from the slurry being hardened. Cement can also be called concrete, which can be used synonymously with cement in this disclosure.

A casing string is tubing that is set inside a drilled wellbore 12 to protect and support production of fluids to the surface 16. In addition to providing stabilization and keeping the sides of the wellbore 12 from caving in on themselves, the casing string can protect fluid production from outside contaminants, such as separating any fresh water reservoirs from fluids being produced through the casing. Also known as setting pipe, casing a wellbore 12 includes running pipe (such as steel pipe) down an inside of the recently drilled portion of the wellbore 12. The small space between the casing and the untreated sides of the wellbore 12 (generally referred to as an annulus) can be filled with cement 32*a*-*e* to permanently set the casing in place. Casing pipe can be run from a floor of the rig 18, connected one joint at a time, and stabbed into a casing string that was previously inserted into the wellbore 12. The casing is landed when the weight of the casing string is transferred to casing hangers which are positioned proximate the top of the new casing, and can use slips or threads to suspend the new casing in the wellbore 12. A cement slurry can then be pumped into the wellbore 12 and allowed to harden to permanently fix the casing in place. After the cement has hardened, the bottom of the wellbore 12 can be drilled out, and the completion process continued.

Sometimes the wellbore 12 is drilled in stages. Here, a wellbore 12 is drilled to a certain depth, cased and cemented, and then the wellbore 12 is drilled to a deeper depth, cased and cemented again, and so on. Each time the wellbore 12 is cased, a smaller diameter casing is used. The widest type of casing can be called conductor casing 20, and is usually about 30 to 42 inches in diameter for offshore wellbores and 12 to 16 inches in diameter for onshore wellbores 12. An annular space 82 radially outside the Conductor casing string 20 can be filled with cement 32*a* to prevent drilling fluids from circulating outside the casing string 20 and causing erosion. The next size in casing strings can be referred to as the surface casing 22, which can run several thousand feet in length. An annular space 80 radially outside the Surface casing string 22 can be filled with cement 32*b* to prevent hydrocarbon fluids from encroaching into fresh water zones. In some wellbores 12, intermediate casing 24 can be run to separate challenging areas or problem zones, such as areas of high pressure or lost circulation. An annular space 78 radially outside the Intermediate casing string 24 can be at least partially filled with cement 32c to isolate formations which can possibly breakdown and cause a loss of circulation in the wellbore.

Generally, the last type of casing string run into the wellbore 12 is the production casing string 26, and is therefore the smallest diameter casing string. The production casing string 26 can be run directly into the producing reservoir 15. An annular space 74 radially outside the Production casing string can be at least partially filled with cement 32e to stop hydrocarbons from migrating to thief zones and to prevent sloughing of formations which can cause circulation loss in the wellbore 12. Additionally, a liner string 34 can be run into the wellbore 12 instead of a casing string. While a liner string 34 is very similar to other casing strings in that it can be made up of separate joints of tubing, the liner string 34 is not run the complete length of the wellbore 12. A liner string 34 can be hung in the wellbore 12 by a liner hanger (not shown), and then an annular space 76 radially outside the liner string 34 can be at least partially filled with cement 32d. A production string 28 can then be run in the wellbore 12 to produce fluids from the producing zone 15 to the surface 16 and the rig 18.

A logging facility 44 can collect measurements from the logging tool 50, and can include processing circuitry 45 for processing and storing the measurements gathered by the logging tool 50. The processing circuitry 45 can be used to determine the integrity of cement 32a-e from the measurements received from the logging tool 50.

Figure 2:
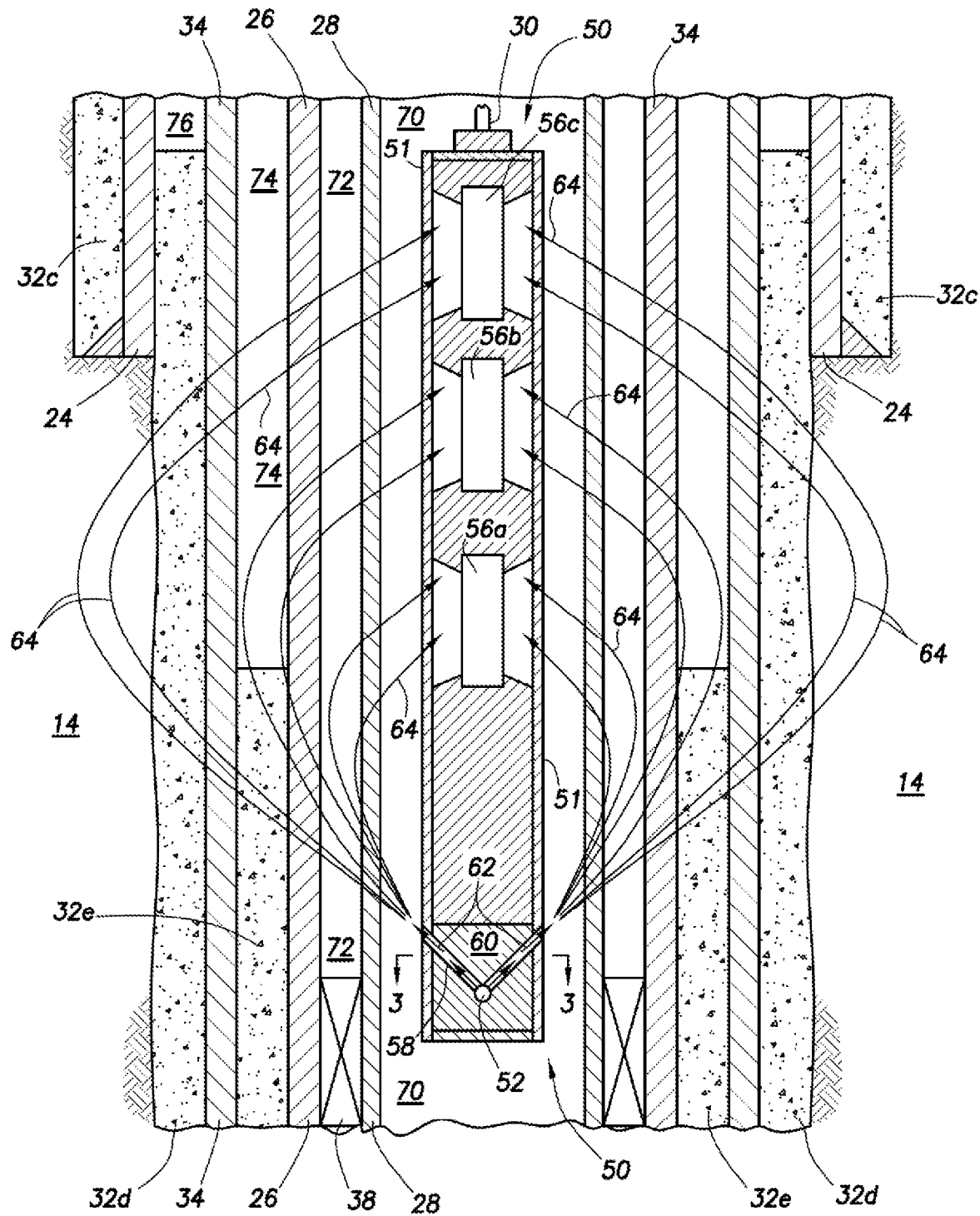
FIG. 2 is a representative partial cross-sectional view of a portion of the multiple-casing wellbore with a three detector logging tool extended into the wellbore on a conveyance.

FIG. 2 shows a logging tool 50 positioned at a desired location in the wellbore 12 and surrounded by multiple casings 24, 34, 26. The other casings 20 and 22 shown in FIG. 1 are not shown here, but measurements can be taken for these and other casings by repositioning the logging tool 50 in the wellbore 12 and reconfiguring the logging tool 50 for the various casing strings. Therefore, the following discussion can be applied to various other configurations of casing strings that have been cemented in the wellbore 12 by positioning the logging tool 50 at various positions in the wellbore 12 as well as using different configurations of the logging tool 50 to evaluate an integrity of cement at various radial depths from the center of the wellbore 12. The example logging tool 50 shown in FIG. 2 includes one photon source 52 and three photon detectors 56a-c, where each of the three detectors 56a-c are at a different longitudinal spacing from the source 52. As used herein, related to spacing between a source 52 and a detector 56 of the logging tool 50, "longitudinal" spacing, distance, or length refers to a distance along a longitudinal axis of the logging tool 50 from the source 52 or 54 to a detector 56a-c.

A longitudinal spacing between the detector 56 and source 52, as well as the energy level of photons 62 emitted from the source 52, can determine the radial depth of investigation (DOI) of photons 64 that are scattered by materials (i.e. production string, casing string, cement, earthen formation, etc.) surrounding the logging tool 50. Generally, an increased distance between the source 52 and a detector 56a-c, increases a radial DOI, and a decreased distance between the source 52 and a detector 56a-c, decreases a radial DOI. Additionally, increased energy level of the source 52 increases a radial DOI, and decreased energy level of the source 52 decreases a radial DOI. Therefore, the actual radial DOI is generally determined by the detector/source spacing, the energy level of the source, and the material through which the photons 62 must travel to be received by one of the detectors 56a-c. By tailoring these variables (such as longitudinal detector/source spacing), the radial DOI can be tailored to evaluate the cement 32 associated with the various casing strings in a wellbore, such as wellbore 12. Please note that various example configurations of sources 52, 54 and detectors 56a-c are shown in FIGS. 4A-6. Multiple detectors shown in the Figures may be indicated as 56a, 56b, 56c, etc., however, this is merely to aid in the discussion of the logging tool 50 and does not imply that these detectors are different. The variously cited detectors 56 can be the same detector type, can be a mix of different and same detector types, can all be different detector types, etc. Any detector capable of detecting photons 64 scattered by the materials in the wellbore 12 may be a suitable detector 56 for the logging tool 50.

The scattered photons 64 are generally shown as arced lines generated from the source 52 and terminated at the various detectors 56a-c. However, the arced lines merely indicate a general migration of the scattered photons 64 toward the detectors 56a-c through surrounding material. Not all photons 62 emitted from the source 52 will be scattered back to the detectors 56a-c as scattered photons 64. Therefore, not all scattered photons 64 will travel the paths suggested by the arched lines. It should be understood, that the actual paths of the scattered photons 64 are much more erratic and random than the paths indicated by these arced lines. The arced lines also indicate a radial DOI from the logging tool 50 of the photons 64. As seen in FIG. 2, the greatest radial DOI can be achieved by a source 52/detector 56 pair with the farthest longitudinal spacing between them.

Conversely, the smallest radial DOI can be achieved by a source 52/detector 56 pair with the shortest longitudinal spacing between them. However, the energy level of the source also plays a minor role in determining the radial DOI of the source 52/detector 56 pair. Thus, it may be possible that the radial DOI can be increased with a decreased longitudinal detector/source spacing if the energy level of the source 52, 54 is sufficiently increased to overcome the reduced spacing. Additionally, it may be possible that the radial DOI can be decreased with an increased longitudinal detector/source spacing if the energy level of the source 52, 54 is sufficiently decreased to negate the effects of the increased spacing. However, it appears that the major determining factor for the radial DOI is the detector/source spacing. If there is but one source 52 or 54, with multiple detectors 56a-c in the logging tool 50, then the radial DOI can be seen as directly proportional to the longitudinal detector/source spacing.

Figure 3:
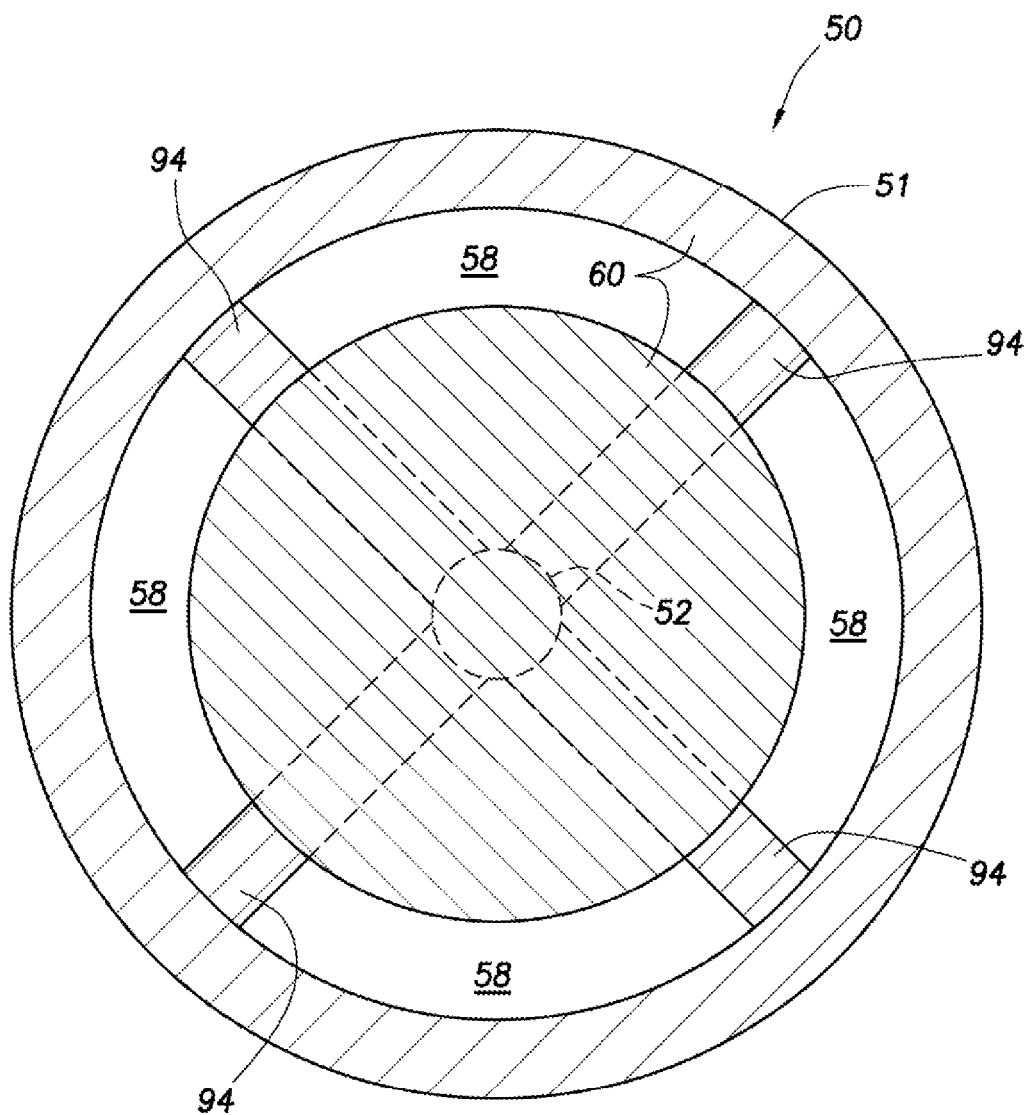
FIG. 3 is cross-sectional view of a bottom portion of the logging tool shown in FIG. 2.

A body 51 of the logging tool 50 can be configured to launch photons 62 from the source 52, 54 through channels 58, which are angled in a direction toward the detectors 56. The channels 58 are formed in an insulating material 60 which prevents photons 62 from traveling directly from the source 52, 54 to a detector 56, and causes the photons 62 to travel along the channels 58 formed in the insulating material 60 of the logging tool 50. Referring to FIGS. 2 and 3, it can be seen that the channels 58 can generally form a 360 degree exit path from the source 52, 54 for the photons 62 as they are emitted from the source. FIG. 3 shows a cross-section of the bottom of the logging tool 50. The insulating material 60 is formed in two major sections, one that is a conical shape that is fit into an inverted conical shape with ribs 94. The ribs 94 can be spaced around the conical surfaces of the two major sections to provide support for the assembly and to define the channels 58 that provide a 360 degree exit path for the photons 62 (possibly minus the space required for the ribs 94). It should be understood that the ribs 94 are merely one example for holding the two sections of the material 60 spaced apart to form the angled channels 58. The channels 58 can be one conically shaped channel 58 without ribs 94. External supports spaced around the body of the tool 50 can be used to secure the two sections in the desired spaced apart position. The source 52 (or 54) can be positioned at the peak of the conical shape, thereby allowing 360 degrees of emission of the photons 62 from the source 52 (or 54), minus the photons effected by the support material (i.e. ribs 94, external supports (not shown), etc.). This can result in a substantially cone-shaped field of photons radiated from the source 52, 54. It should also be understood that the ribs 94 and external supports can be made from material(s) (e.g. titanium, etc.) that are semi-transparent to the flow of photons from the source 52, 54, thereby allowing a full 360 degree exit path for the collimated photons 62 from the tool 50.

Furthermore, the illustration in FIG. 3 is merely an example of a source structure design which can provide panoramic emission of high energy photons. Any source structure that allows high energy gamma rays (or high energy photons) homogeneously emitted outside the tool body 51 can be adopted for the design of a photon source. For example, if only one channel 58 in FIG. 3 allowed photons to be emitted from the tool 50, with the other three channels 58 being replaced by photon insulating material 60, then the tool 50 and/or the structure containing the source could be rotated to provide a 360 degree panoramic coverage of emitting photons into the wellbore environment. Alternatively, or in addition to, the bottom portion of the tool 50 can be rotated without rotating the whole tool 50 to produce the desired 360 degree emission of the photons 62.

Referring again to FIG. 2, photons 62 emitted from the source 52 can travel through the channels 58 and be launched into material surrounding the logging tool 50. The photons 62 are scattered by the surrounding material producing scattered photons 64 which travel through the surrounding material to then be collected by detectors 56a-c. Each detector 56a-c has near 360 degree accessibility for receiving photons 64 from the surrounding material (i.e. casing strings 20, 22, 24, 26, 34, production string 28, cement 32a-e, earthen formation 14, material in annuli 70, 72, 74, 76, 78, 80, 82, etc.). The detectors 56a-c can determine photon count rates of received photons 64, by counting all received photons regardless of the energy level of the photon 64, and/or they can determine photon count rates for received photons with an energy level within a desired energy range. For detecting integrity of cement 32a-e, it is preferred to count all received photons 64 and produce a count rate that includes all detected photons 64 regardless of energy level. This provides a greater number of photons contributing to the count rates and can improve the accuracy of determining cement integrity. However, it should be understood, that cement integrity can also be determined using count rates that group detected photons 64 into energy ranges.

In the example of FIG. 2, the logging tool 50 can use the detector 56a, 56b, 56c to determine presence and/or absence of cement just outside of the production casing string. The tool 50 is preferably centered in the production string 28 by any means that centralizes the tool, such as centralizers (not shown). The longitudinal detector/source spacing and the energy level of the source 52 have been adjusted such that the detector 56a preferentially collects photons 64 traveling through near wellbore environment, such as production tubing 28, the annulus 72, and the production casing 26. Similarly, the longitudinal detector/source spacing and the energy level of the source 52 have been adjusted such that the detector 56b can be used to evaluate the integrity (such as presence or absence of cement in the associated annulus) of the cement 32e in the annulus 74. As can be seen, the photons 64 that travel along the arched lines to the detector 56b may be used to evaluate the integrity of the cement 32e in the annulus 74 radially outside casing 26. As the tool 50 would travel along the production string 28, the detector 54b can detect the presence and/or absence of cement 32e in the annulus 74. Therefore, the detector 54b should be able to detect the transition between the absence of cement 32e in the annulus 74 to the presence of cement 32e as shown in FIG. 2. Additionally, the detector 56c may be used to evaluate the integrity of cement 32d in annulus 76 radially outside casing 34 (or liner 34) and possibly also the integrity of cement 32c in annulus 78 radially outside casing 24. If deeper radial evaluations are desired, then another example of the tool 50 can be tailored for an increased radial DOI to measure cement 32b, 32a integrity in the annuli 80 and 82 outside of the casings 22 and 20, respectively. The scattered photons 64 can also be used to determine if cement 32a-e has fissures, voids, breakages, or anomalies other than cement with its desired consistency and structural integrity.

FIGS. 4A-4C are example configurations of the logging tool 50 which can be used in various wellbore 12 configurations to evaluate various radial DOI's. Referring to FIG. 4A, the example logging tool 50 includes one source 52 and three detectors 56a-c. Photons 62 are emitted from the source 52 through channels 58 as a cone-shape and into the surrounding materials. Again, it should be understood that the tool 50 can produce 360 degree coverage of emitting photons 62 by rotating the tool 50 and/or the structure containing the source, thus producing a panoramic distribution of the emitted photons 62. The dashed lines are similar to the arched lines in FIG. 2 in that they generally represent paths of scattered photons 64 that migrate to the detectors 56a-c. The body 51 again should include an insulating material 60 (not shown here, refer to FIG. 2) that bounds the channels 58, thus causing the photons 62 to exit the tool 50 in a slightly angled trajectory. The angle of the trajectory can be generally determined by the angle A of the channel 58 when referenced to an axis perpendicular to the center axis 88 of the tool 50. This angle of trajectory can also influence the radial DOI of the scattered photons 64. The three detectors 56a-c are shown spaced apart from the source 52 at lengths L1, L2, and L3, respectively. These lengths are adjusted as necessary to achieve the desired radial DOI for each detector/source pair (e.g. detector 56a/source 52, detector 56b/source 52, detector 56c/source 52).

Referring to FIG. 4B, the example logging tool 50 includes two sources 52, 54 and three detectors 56a, 56b, 56c. In this configuration, the elements are contained within the body 51 of the logging tool 50, with two detector/source sets 53, 55. The first set 53 can be at one end of the tool body 51, and can include the source 52 and detectors 56a, 56b. The second set 55 can be at the opposite end of the tool body 51, and can include the source 54 and a detector 56c. The two sets 53, 55 are isolated from each other by a photon insulating material 90 positioned in the body 51 between the first and second detector/source sets 53, 55. The insulating material 90 helps to minimize cross-talk or cross-interference between the two sets 53, 55. Again the sources 52, 54 emit photons through channels 58 which are slightly angled by angle A. Angle A is shown for both sources, but it should be understood, that angle A can be different values for the sources 52, 54. It is not a requirement that these angles be the same value. In this example, the channels 58 for each source 52, 54 are slightly angled toward each other with the detectors positioned between the two sources 52, 54. Again, it is not required for these elements of the tool 50 to be oriented as shown in FIG. 4B. This is merely an example of possible orientations for these elements. The detector 56c is spaced longitudinally away from the source 54 by the length L6, with the detectors 56a, 56b spaced longitudinally away from the source 52 by the lengths L4, L5, respectively. Again the dashed lines represent a general trajectory of the photons 64 as they travel through the surrounding material before being detected by the detectors 56a, 56b, 56c. The two sources 52, 54 are shown spaced longitudinally away from each other by the length L7. This distance L7 can help minimize interference between the detector/source sets 53, 55.

Referring to FIG. 4C, the example logging tool 50 can include two sources 52, 54 and three detectors 56a, 56b, 56c. This configuration can also contain two detector/source sets 53, 55 with each set contained in a separate body 5151a, 51b, and where each body 51a, 51b can be connected together via the connector 92. This configuration allows for multiple tool configurations to be easily connected together into one tool 50 via the connector 92. A material 90 can be positioned proximate or within the connector 92 to further reduce interference of photons 62 between the two sets 53, 55. The first set 53 can be in body 51a at one end of the tool 50, and can include the source 52 and detector 56a, 56b. The second set 55 can be in body 51b at an opposite end of the tool 50, and can include the source 54 and a detector 56c. Again the sources 52, 54 can emit photons 62 through channels 58 which are slightly angled by angle A, and are angled in the same direction, unlike the tool 50 in FIG. 4B where the channels 58 are angled toward each. The detector 56c is spaced longitudinally away from the source 54 by the length L8, with the detectors 56a, 56b spaced longitudinally away from the source 52 by the lengths L10, L11, respectively. The two sources 52, 54 are shown spaced longitudinally away from each other by the length L9. These FIGS. 4A-4C show various example configurations of the logging tool 50, but many other configurations are possible.

Figure 5:
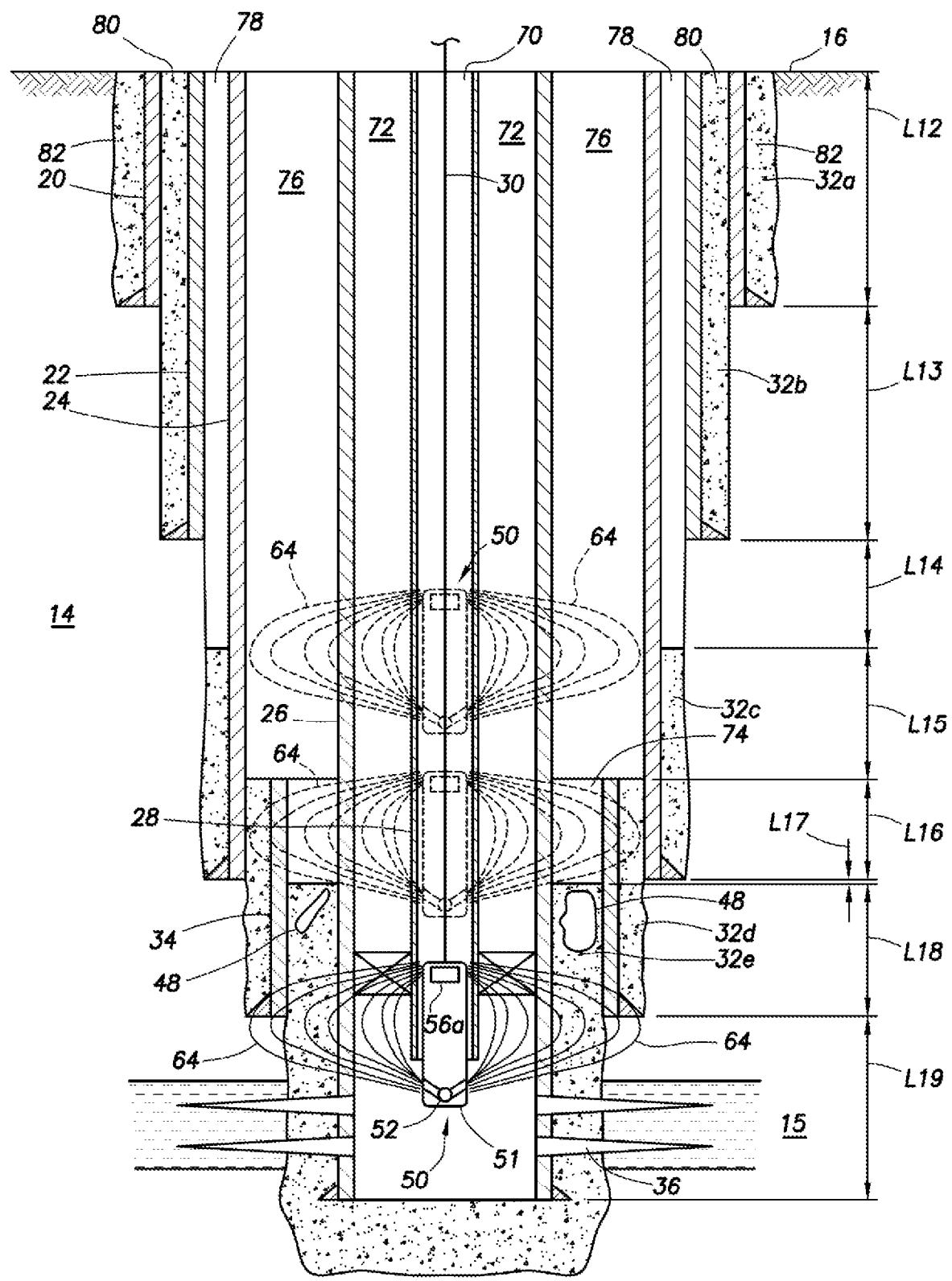
FIG. 5 is a representative partial cross-sectional view of the multiple-casing wellbore with another example logging tool extended to various positions in the wellbore.

FIG. 5 shows a wellbore 12 with multiple casing strings 20, 22, 24, 26, 34, and a production string 28, which have been generally described above. Each of the casing strings 20, 22, 24, 26, 34 are secured in the wellbore 12 by cement 32 that fills at least a portion of an annulus radially outside of the casing strings 20, 22, 24, 26, 34. For example, cement 32a can fill the annulus 82 which is radially outside the casing string 20. Cement 32b can fill the annulus 80 which is radially outside the casing string 22. Cement 32c can fill a portion of the annulus 78 which is radially outside the casing string 24. Cement 32d can fill the annulus 76 which is radially outside the casing string (or liner) 34. Cement 32e can fill a portion of the annulus 74 which is radially outside the casing string 26. Perforations 36 can penetrate the cement 32e and extend into the production zone 15. The logging tool 50 can be configured to evaluate any one or more of the cements 32a-e. The logging tool 50 in FIG. 5 has been configured to evaluate the cements 32d and 32e, but may not be well suited for evaluating the other cements 32a-c. This shows that each tool 50 can be specifically tailored to evaluate specific radial distances.

The top position of the tool 50 shows photon 64 paths (i.e. curved dashed lines) to extend into the annulus 76 in an area where no cement 32d or 32e is present. Therefore, the scattered photon counts collected by the detector 56 would indicate the absence of cement in these radial positions. The second (or middle) position of the tool 50 shows photon 64 paths (e.g. curved dashed lines) that continue to extend into the annulus 76 and the annulus 74, where the collected scattered photons can indicate the absence of cement 32e in the annulus 74, but the presence of cement 32d in the annulus 76. The third (or lowest) position of the tool 50 shows photon 64 paths (e.g. curved solid lines) that continue to extend into the annulus 76 and the annulus 74, where the collected scattered photons can indicate the presence of cement 32e in the annulus 74, and possible the presence of cement 32d in the annulus 76 and/or the earthen formation 14 at the radial position of the annulus 76.

At each of the positions where the cement is expected, then the count rates of the scattered photons 64 collected by the detector 56 can be used to determine the integrity of the cement through which the photons 64 are scattered. For example, a place of reduced integrity 48, such as a void, in the cement 32e can cause different photon count rates from expected count rates when the tool 50 is positioned proximate the reduced integrity 48. This difference in the count rates can be used to determine that the cement 32e has an area that is void 48 of cement 32e. Similarly, fissures, fractures, etc. in the cement 32a-ecan cause varied count rates from the expected count rates. It should be understood, that the expected count rates can be generated in the lab under controlled testing conditions that approximate the wellbore conditions, and/or via simulations of the tool 50 and the wellbore conditions. Therefore, variations from the expected count rates can indicate that actual wellbore conditions are different from the expected conditions. The differences in the count rates can be evaluated to determine the extent of the differences in the actual wellbore conditions. In addition, other mathematical methods can be applied to construct a signal from count rates. For example, the signal could be a ratio of count rates from the two detectors, a logarithmic of the ratio, etc. Any deviation from a signal of expected conditions can indicate a variation in the wellbore condition. The lengths L12-L19 represent various longitudinal distances along the wellbore 12 of boundary conditions between the different casing strings 20, 22, 24, 26, 34 and between different cemented locations.

Figure 6:
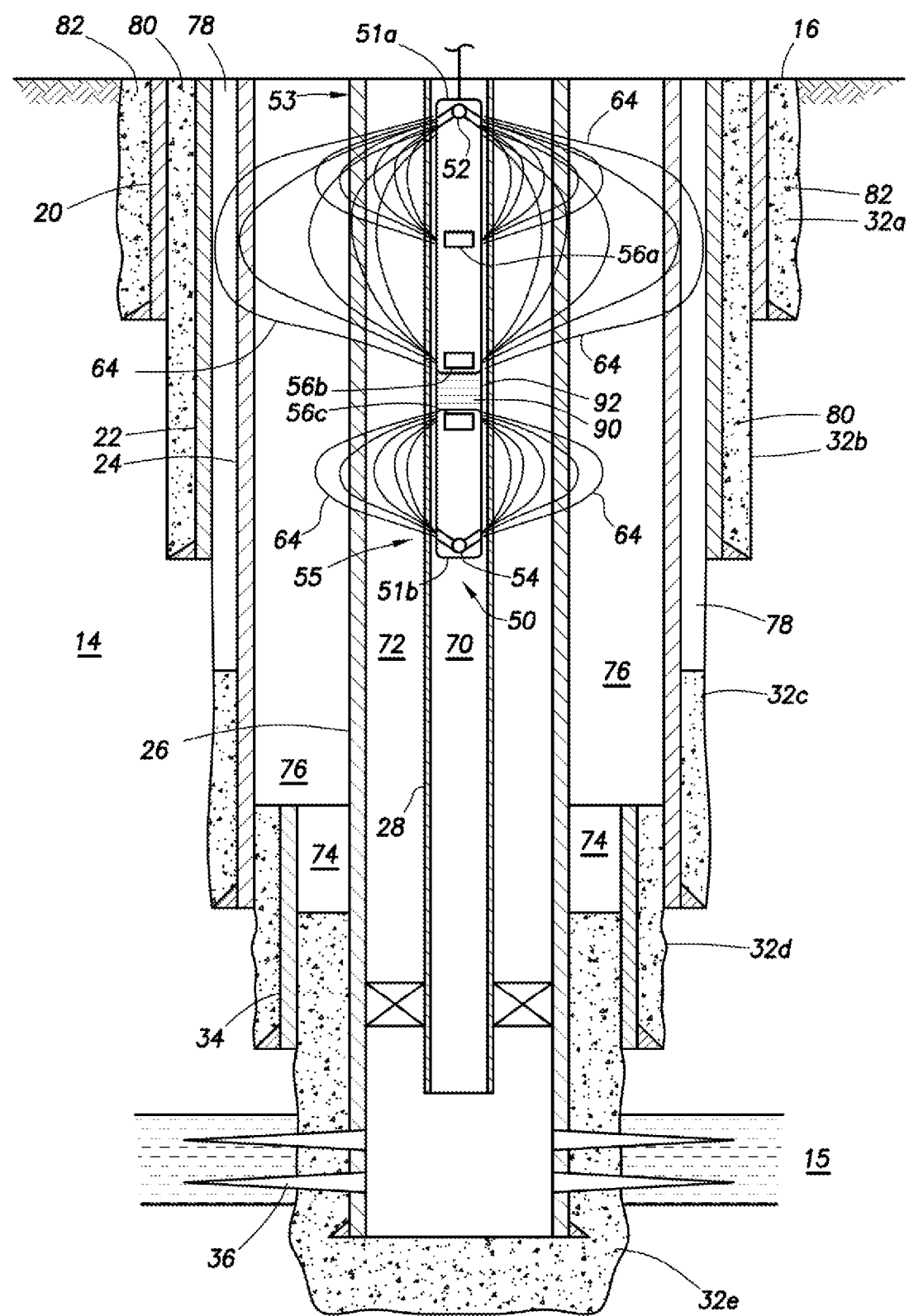
FIG. 6 is another representative partial cross-sectional view of the multiple-casing wellbore with yet another example logging tool extended into the wellbore.

FIG. 6 shows another example logging tool 50 which includes two detector/source sets 53, 55, similar to the logging tool 50 in FIG. 4B. The first set includes source 52 and detectors 56a, 56b positioned in body 51a of the tool 50 and connected to lower body 51b of the tool 50 via a connector 92. It should be understood that additional detector/source sets may be connected to the tool 50 via additional connectors 92. Each connector region can include (or be made from) a photon insulating material 90 to help reduce photon interference between detector/source sets. The upper portion of the tool 50 can include that source 52 and detectors 56a, 56b. The photon 64 paths (i.e. curved solid lines) associated with each source/detector pair indicates the various radial DOI for each pair. The detector 56b/source 52 pair has been tailored to produce a radial DOI that extends into the cement 36b and possibly the cement 32a, as where the detector 56a/source 52 pair can produce a radial DOI that extends generally to the cement 32d, and the radial DOI of the detector 56c/source 54 pair may extend generally to the cement 32e. It should be understood that photons 64 for each of these pairs may travel into the outer cement layers and return back to the detectors. However, different detector/source pairs can provide different sensitivities to different radial distances from the center of the wellbore 12. In other words, the radial sensitivities for each detector/source pair can be tailored to be more sensitive to the desired radial DOI. Therefore, the reduced integrity 48a may be more easily detected using the detector 56b/source 52 pair than the other two pairs shown in FIG. 6. Additionally, the reduced integrity 48b may be more easily detected using the detector 56c/source 54 pair than the other two pairs, even though the detector 56a/source 52 may also provide significant sensitivity to the reduced integrity 48b to facilitate detection of the reduced integrity 48b.

The detector 56c/source 54 set in the lower body 51b of the tool 50 can include a low energy source that is a Cs-137 source with an emission peak at 0.662 MeV. This Cs-source can be used for either one or both of the sources 52, 54 (or any other source not shown). In the tool 50 example of FIG. 6 the lower set 55 may employ the Cs-source since it is being tailored for a shallower radial DOI. Additionally, the upper set 53 of the tool 50 may include a high energy source that can be a Co-60 source with an emission peak at either 1.332 Mev or 1.17 Mev. The upper set 53 may employ the Co-source since it is being tailored for a deeper radial DOI. The varied spacing of the detectors can provide additional radial DOI tailoring. It should be understood that the Cs- and Co-sources are merely examples of the photon sources 52, 54, but other sources can also be used in the tool 50.

The Cs-source 54 can be optimized to mainly be sensitive to the surrounding material between a front of the tool 50 and an inner surface of intermediate casing 24, which can include the production string 28, production casing 26, and the cement 32e, as well as the liner 34 and its associated cement 32d. The detector to source spacing of approximately 8 inches can be used to produce this radial sensitivity using the Cs-source. The upper set 53 of the tool 50 may utilize the Co-source to provide higher energy photons 62. The two detectors 56a, 56b can be placed sufficiently apart from the Co source 52, such that detector 56a is closer to the source 52 so that it has measurement range up to an inner surface of surface casing 22, which may include the cement 32c. The detector to source spacing of approximately 12 inches can be used to produce this radial sensitivity using the Co-source. The detector 56b can be father away from the source 52 so that it has a measurement range up to an inner surface of the conductor casing 20, including the cement 32b. The detector to source spacing of approximately 15 inches can be used to produce this radial sensitivity using the Co-source. Again, a wide range of tool 50 configurations can be used to provide these desired radial sensitivities other than the ones explicitly shown in this disclosure.

Figure 7:
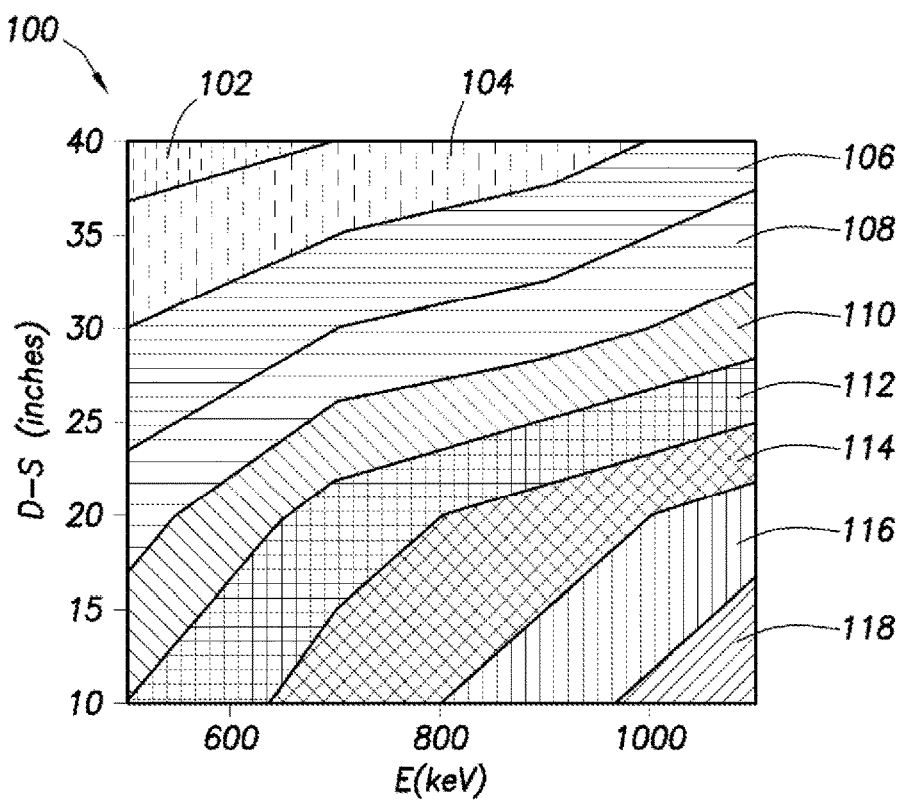
FIG. 7 is a representative chart of detected photon count rates plotted as a function of a distance (measured between a photon detector and a photon source) and an energy level of photons emitted from the source.

FIG. 7 shows a chart 100 that indicates count rates plotted as a function of detector-source spacing (D-S in inches) vs. an energy level of the source (E in keV). The chart regions 102-118 indicate count rates of photons 64 detected for various energy ranges by a detector 56 with different source-detector spacing. The region 102 corresponds to a combination of low source energy and high source-detector spacing, which can translate to a small number of detected photons that have traveled through the surrounding material in the wellbore 12. The region 118 corresponds to a combination of high source energy and small source-detector spacing, which can translate to a large number of detected photons that have traveled through the surrounding material in the wellbore 12. As illustrated in FIG. 7, a high source energy can increase the number of photons detected at the detector placed at a far source-detector spacing.

Figure 8:
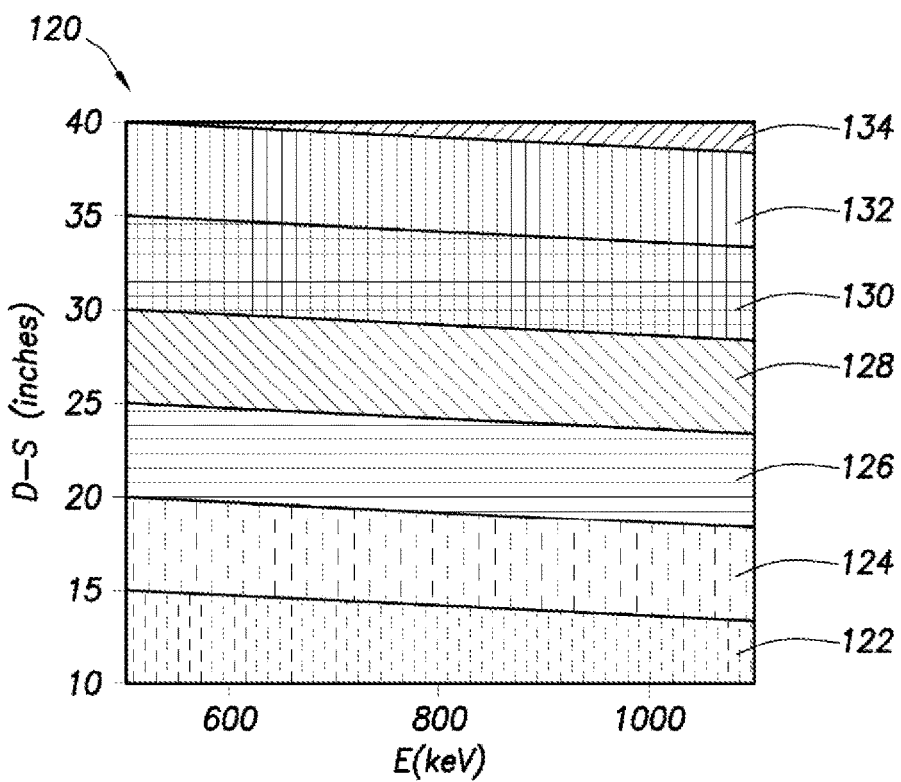
FIG. 8 is a representative chart of various radial depths of investigation plotted as a function of a distance (measured between a photon detector and a photon source) and an energy level of photons emitted from the source.

However, it should be noted that FIG. 8 indicates that the detector to source spacing primarily determines the radial DOI, with increased source energy providing small changes in the radial DOI. Additionally, a source 52, 54 with a high energy output increases the amount of count rates detected by the detectors 56. The regions 122-134 indicate radial DOI with region 112 being the shallowest radial DOI and region 134 being the deepest radial DOI.

FIGS. 9 and 10 show count rates detected from a Cs-source 52, 54 (FIG. 9) and from a Co-source 52, 54 (FIG. 10) for the case where the cement being investigated is present and the case where the cement is not present. Line 144 in the plot 140 in FIG. 9 indicates the count rates of scattered photons 64 used to evaluate cement adjacent a near tubing (like casings 34, 26) where the cement is absent. Line 142 indicates the count rates of scattered photons 64 used to evaluate the cement adjacent the near tubing where the cement is present. Line 154 in the plot 150 in FIG. 10 indicates the count rates of scattered photons 64 used to evaluate cement adjacent the near tubing where the cement is absent. Line 152 indicates the count rates of scattered photons 64 used to evaluate the cement adjacent the near tubing where the cement is present. A high energy source 52, 54 like Co-source may be preferred when the detector 56 is spaced at a sufficiently far distance from the source 52, 54. However, for near tubing regions, a lower source energy, such as from a Cs-source, can provide higher measurement sensitivity to a cement integrity change. Using the Cs-source for this example, there is about a 27% change in the count rates between the cement present and cement absent conditions, while using the Co-source, there is about a 15% change in the count rates between the cement present and cement absent conditions. Therefore, there are many factors that are considered in configuring a tool 50 to evaluate a desired radial DOI.

In general, to obtain information about the cement integrity of cement 32a-e from the full annulus, the detector 56 is preferably not collimated azimuthally (i.e. can receive photons from any azimuthal direction). The source 52, 54 can be substantially collimated in a cone shape towards the detector(s) 56. As used herein, "substantially cone-shaped" refers to a cone shape that may have some spaced apart voids around the circumference of the cone. Therefore, if a cone-shaped channel includes support structures 94 that traverse the channel space, and the structures 94 are circumferentially spaced around the cone-shaped channel 58, then the channel 58 and/or photons 62 radiating through the channel 58 from the peak to the base of the cone can be referred to as being cone-shaped. Therefore the full annulus, substantially 360 degree circumference of the annulus, can be radiated by the emitted photons 62. Additionally, if the source is collimated toward one general azimuthal direction instead of a cone-shape, the area under investigation can be segmented. By rotating the source 52, 54, the tool 50 can provide cement integrity information azimuthally, which can also be used to determine panoramic cement integrity.

This disclosure provides an apparatus for evaluating cement integrity in multi-annuli for a multi-string wellbore 12 configuration. It can utilize two or more sources of different energies to enhance the counting statistics for detectors 56 measuring different cement annuli. The source 52, 54 can be collimated into a cone shape and use non-azimuthally collimated gamma detectors 56 to measure high energy photons scattered back from all directions, which can provide information about a full circumferential cement annulus.

A few methods can be used to evaluate the cement integrity based on the detected count rates of scattered photons 64 by the detectors 56. One method can compare the count rates measured at a certain detector 56 with an expected value for a given wellbore 12 completion profile. Difference can indicate that the cement integrity deviates from the expected cement condition. The expected value can be generated through a lab characterization and/or from benched marked simulation results. Another method can be to derive shallow cement information from a near tubing detector 56 measurement and feed this information into forward modeling of a detector 56 used to measure a larger radial distance. With the near tubing information, the detector 56 and/or computing circuitry 45 can be used to distinguish a near cement annulus from a far cement annulus contribution in a far detector 56 response.

Yet another method can be to use forward modeling. A wellbore 12 completion profile can be constructed based on extensive lab data and simulation data for each detector and its respective measurement region as generally represented by the equation below.

$$CR_i = f(cement_i, casing_i)$$

Using an inversion process to minimize the difference between the measured CR and expected CR (CR being count rate), the cement integrity information can be obtained by the equation below.

$$\Sigma |CR_{measured} - CR_i|^2$$

This tool can be run with other wellbore integrity evaluation tools and/or use an output from other tools from previous runs, for example the casing thickness information from an EM corrosion tool or an acoustic tool.

Thus, a logging tool 50 for evaluating an integrity of cement 32 in a wellbore 12 with multiple casing strings 20, 22, 24, 26, 34 is provided and the tool 50 may include a first body 51, 51a and a first detector/source set 53 contained in the first body 51, 51a. The first set 53 can include at least a first collimated photon source 52 that produces a substantially cone-shaped field of photons 62 emitted from the first source 52, and at least a first non-azimuthally collimated photon detector 56a spaced away from the first photon source 52 by a first distance L4, L10. The first distance L4, L10 can configure (along with the energy level of the source 52) the tool 50 such that the first source 52 photons 62 travel to a first annulus 72-82 positioned radially outside a first casing string 20, 22, 24, 26, 34, with at least a portion of the first source 52 photons 62 that travel into the first annulus 72-82 and are scattered back to the first detector 56a. The first detector 56a can be configured to receive the scattered photons 64 from the first annulus 72-82 and produce photon count rates based on energy levels of the first source 52 scattered photons 64 that are received by the first detector 56a. A presence or absence of cement 32 in the first annulus 72-82 can be determined by the first detector 56a count rates, by comparing these first detector 56a count rates with expected count rates for the first annulus 72-82. The expected count rates can be determined by prior collected data, computer simulation of the wellbore 12, etc. The first detector 56a can be configured to simultaneously receive scattered photons 64 from the first annulus 72-82 at substantially any azimuthal direction around a circumference of the first detector 56a.

For any of the foregoing embodiments, the tool, system or method may include any one of the following elements, alone or in combination with each other:

The tool 50 can include a detector 56a and/or processing circuitry that compares the first detector 56a count rates to expected count rates for the first annulus 72-82, and can determine the presence of cement 32 in the first annulus 72-82 and can determine a reduced integrity 48 of the cement 32 in the first annulus 72-82 based on the comparison. The reduced integrity 48 can be selected from a group consisting of a void, a fracture, a fissure, a crack, an area of erosion, an area of degradation, and any combination thereof. The tool 50 can further include a second non-azimuthally collimated photon detector 56b spaced away from the first source 52 by a second distance L5, L11. The second distance L5, L11 can configure the tool 50 such that the first source 52 photons 64 travel to a second annulus 76-82 positioned radially outside a second casing string 20, 22, 24, 34, where at least a portion of the first source 52 photons 64 that travel into the second annulus 76-82 are scattered back to the second detector 56b that is configured to receive the scattered photons 64 from the second annulus 76-82. "Configuring the tool" refers to positioning a detector a desired distance from a photon source such that the desired radial Depth Of Investigation (DOI) for evaluating one or more of the annuli outside of each one of the multiple casing strings in the wellbore. Increased distance from the source can increase the radial DOI, and decreased distance from the source can decrease the radial DOI. Changing the energy level of the photon source can also impact the radial DOI, but the impact can be minimal.

Second detector 56b count rates can be produced by the second detector 56b based on energy levels of the first source 56a photons 64 that are received by the second detector 56b. A presence or absence of cement 32 in the second annulus 76-82 can be determined by a comparison of the second detector 56b count rates to expected count rates for the second annulus 76-82. The presence of cement 32 in the second annulus 76-82 can be determined by the comparison, and a reduced integrity 48 of the cement 32 in the second annulus 76-82 can also be determined by the comparison. Again, the reduced integrity 48 of the cement 32 in the second annulus 76-82 can be selected from a group consisting of a void, a fracture, a fissure, a crack, an area of erosion, an area of degradation, and any combination thereof.

The second annulus 78-82 can be radially outside the first annulus 76-80. Additionally, a third annulus 74-78 can be radially inside the first and second annuli 76-82. Fourth and fifth annuli 72-76 can be radially inside the third annulus 74-78, or radially outside the second annulus 78-82. One or more centralizers can be used to position the first photon source 52, the first photon detector 56a, and the second photon detector 56b proximate a center of a tubing string 28 through which the tool 50 is run into the wellbore.

The tool 50 can also include a second detector/source set 55 with a second collimated photon source 54 that can produce a substantially cone-shaped field of photons 62 emitted from the second source 54, and a third non-azimuthally collimated photon detector 56c spaced away from the second photon source 54 by a third distance L6, L8, where the third distance L6, L8 can configure the tool 50 such that photons 64 from the second source 54 travel to the third annulus 74-78 positioned radially outside a third casing string 22, 24, 26, 34, with at least a portion of the second source 54 photons 64 that travel into the third annulus being scattered back to the third detector 56c which is configured to receive the scattered photons 64 from the third annulus 74-78.

The photon count rates produced by the third detector 56c can be based on energy levels of the second source 54 scattered photons 64 that are received by the third detector 56c, and a presence or absence of cement 32 in the third annulus 74-78 can be determined by the third detector 56c count rates. A comparison of the third detector 56c count rates to expected count rates for the third annulus 74-78 can determine the presence of cement 32 in the third annulus 74-78 and can determine a reduced integrity 48 of the cement 32 in the third annulus 74-78. The reduced integrity 48 of the cement 32 in the third annulus 74-78 can be selected from a group consisting of a void, a fracture, a fissure, a crack, an area of erosion, an area of degradation, and any combination thereof.

The second detector/source set 55 can be contained in the first body 51, 51a with the first set 53 and spaced apart from the first detector/source set 53, with a photon insulating material 90 positioned in the first body 51, 51a between the first and second sets 53, 55. The insulating material 90 and the spacing between the first and second sets 53, 55 can minimize interference between the first and second sets 53, 55. The second detector/source set 55 can also be contained in a second body 51b of the tool 50, where the second body 51b is connected to the first body 51a via a connector 92. The second detector/source set 55 can be spaced apart from the first detector/source set 53 and a photon insulating material 90 can be positioned in the connector 92 of the second body 51b, where the insulating material 90 and the spacing between the first and second sets 53, 55 can minimize interference between the first and second sets 53, 55.

A system 10 for evaluating integrity of cement 32 in a wellbore 12 with multiple casing strings 20, 22, 24, 26, 34 is provided. The system 10 may include a logging tool 50 with a first body 51, 51a and a first detector/source set 53 contained in the first body 51, 51a. The system 10 may also include a conveyance 30 used to run the logging tool 50 into and out of the wellbore 12, as well as locate the logging tool 50 at various desired locations along the wellbore 12. The tool 50 can include a first photon source 52 contained in the first body 51, 51a that produces a substantially cone-shaped field of photons 62 emitted from the first source 52, and a first photon detector 56a contained in the first body 51, 51a and spaced away from the first photon source 52 by a first distance L4, L10 that configures the tool 50 such that the first source 52 photons 64 travel to a first annulus 72-82 positioned radially outside a first casing string 20, 22, 24, 26, 34, with at least a portion of the first source 52 photons 64 that travel into the first annulus 72-82 and are scattered back to the first detector 56a that is configured to receive the scattered photons 64 from the first annulus 72-82. Photon count rates produced by the first detector 56a can be based on energy levels of the scattered photons 64 from the first source 52, where the first source 52 scattered photons 64 are received by the first detector 56a, and a presence or absence of cement 32 in the first annulus 72-82 can be determined by the first detector 56a photon count rates.

For any of the foregoing embodiments, the system may include any one of the following elements, alone or in combination with each other:

The first detector/source set 53 can further include a second photon detector 56b spaced away from the first source 52 by a second distance L5, L11. The second distance L5, L11 configures the tool 50 such that the first source 52 photons 64 travel to a second annulus 76-82 positioned radially outside a second casing string 20, 22, 24, 34, and at least a portion of the first source 52 photons 64 that travel into the second annulus 76-82 are scattered back to the second detector 56b that is configured to receive the scattered photons 64 from the second annulus 76-82. The second detector 56b can be configured to simultaneously receive scattered photons 64 from the second annulus 76-82 at substantially any azimuthal direction around a circumference of the second detector 56b.

The second detector 56b count rates produced by the second detector 56b can be based on energy levels of the first source 52 photons 64 that are received by the second detector 56b. A presence or absence of cement 32 in the second annulus 76-82 can be determined by a comparison of the second detector 56b count rates to expected count rates for the second annulus 76-82. The comparison can determine the presence of cement 32 in the second annulus 76-82, and can further determine integrity of the cement 32 in the second annulus 76-82. The integrity of the cement 32 in the second annulus 76-82 may include one of a void, a fracture, a fissure, a crack, an area of erosion, an area of degradation, and any combination thereof (reduced integrity 48).

A method for evaluating an integrity of cement 32 in a wellbore 12 with multiple casing strings 20, 22, 24, 26, 34 is provided, where the method can include the operations of positioning a logging tool 50 in the wellbore 12, where the tool 50 can include a first body 51, 51a, and a first detector/source set 53 contained in the first body 51, 51a, the first set 53 including at least a first collimated photon source 52 that produces a substantially cone-shaped field of photons 62 emitted from the first source 52, and at least a first non-azimuthally collimated photon detector 56a spaced away from the first photon source 52 by a first distance L4, L10. The method can further include radiating a first annulus 72-82 with photons 64 from the first source 52, with at least a portion of the first source 52 photons 64 traveling through the first annulus 72-82 and being scattered back to the first detector 56a that is configured to receive the scattered photons 64 from multiple azimuthal directions around a circumference of the first detector 56a from the first annulus 72-82. Producing photon count rates via the first detector 56a based on energy levels of the first source 52 scattered photons 64 received by the first detector 56a, and determining a presence or absence of cement 32 in the first annulus 72-82 based on the first detector 56a count rates.

For any of the foregoing embodiments, the method may include any one of the following elements, alone or in combination with each other:

The first detector 56a can be configured to receive the scattered photons 64 from multiple azimuthal directions around a circumference of the first detector 56a from the first annulus 72-82. Comparing the first detector 56a count rates with expected count rates for the first annulus 72-82 can determine a presence or absence of cement in the first annulus 72-82, and can determine a reduced integrity 48 of the cement 32, where the reduced integrity 48 can be selected from a void, a fracture, a fissure, a crack, an area of erosion, an area of degradation, and any combination thereof. The first detector/source set 53 can further include a second non-azimuthally collimated photon detector 56b spaced away from the first source 52 by a second distance L5, L11.

The method can further include radiating a second annulus 76-82 with photons 64 from the first source 52, with at least a portion of the first source 52 photons 64 traveling through the second annulus 76-82 and being scattered back to the second detector 56b that is configured to receive the scattered photons 64 from multiple azimuthal directions around a circumference of the second detector 56b from the second annulus 76-82. The detectors 56 in this disclosure can be configured to simultaneously receive scattered photons from one or more of the annuli at substantially any azimuthal direction around a circumference of the detector.

Although various embodiments have been shown and described, the disclosure is not limited to such embodiments and will be understood to include all modifications and variations as would be apparent to one skilled in the art. Therefore, it should be understood that the disclosure is not intended to be limited to the particular forms disclosed;

rather, the intention is to cover all modifications, equivalents, and alternatives falling within the spirit and scope of the disclosure as defined by the appended claims.

The invention claimed is:

1. A logging tool for evaluating an integrity of cement in a wellbore with multiple casing strings, the tool comprising:
 a first body; and
 a first detector/source set contained in the first body, the first set comprising:
  at least a first collimated photon source that produces a field of photons emitted from the first source, and
  at least a first non-azimuthally collimated photon detector spaced away from the first source by a first distance that sets a first radial depth of investigation (DOI) of the first detector, with photon count rates produced by the first detector that are based on energy levels of scattered photons received by the first detector from materials surrounding the wellbore.

2. The tool of claim 1, wherein increasing the first distance increases the first radial DOI and decreasing the first distance decreases the first radial DOI, and wherein the field of photons emitted from the first source is one of a substantially cone-shaped field and a panoramic field.

3. The tool of claim 1, wherein the first detector photon count rates indicate a reduced integrity of cement in a first annulus, and wherein the reduced integrity of cement in the first annulus is selected from a group consisting of a void, a fracture, a fissure, a crack, an area of erosion, an area of degradation, and any combination thereof.

4. The tool of claim 1, wherein the first detector/source set further comprises a second non-azimuthally collimated photon detector that is spaced away from the first source by a second distance, and wherein the second distance sets a second radial depth of investigation (DOI) of the second detector, with photon count rates produced by the second detector that are based on energy levels of scattered photons received by the second detector from materials surrounding the wellbore.

5. The tool of claim 4, wherein increasing the second distance increases the second radial DOI and decreasing the second distance decreases the second radial DOI.

6. The tool of claim 4, wherein the second detector photon count rates indicate a reduced integrity of cement in a second annulus.

7. The tool of claim 6, wherein the second annulus is radially outside a first annulus.

8. The tool of claim 7, wherein a third annulus is radially inside the first and second annuli.

9. The tool of claim 4, wherein a third detector is placed at a third distance from the first source, wherein the third distance sets a third radial depth of investigation (DOI) of the third detector, with photon count rates produced by the third detector that are based on energy levels of scattered photons received by the third detector from materials surrounding the wellbore.

10. The tool of claim 1, further comprising a second detector/source set comprising:
 at least a second collimated photon source that produces a field of photons emitted from the second source, and
 at least a fourth non-azimuthally collimated photon detector spaced away from the second photon source by a fourth distance that sets a fourth radial depth of investigation (DOI) of the fourth detector, with photon count rates produced by the fourth detector that are based on energy levels of scattered photons received by the fourth detector from materials surrounding the wellbore.

11. The tool of claim 10, wherein the fourth detector photon count rates indicate a reduced integrity of cement in a fourth annulus.

12. The tool of claim 10, wherein the second detector/source set is contained in the first body and spaced apart from the first detector/source set, wherein a photon insulating material is positioned in the first body between the first and second sets, and wherein the insulating material and the first and second set spacing reduces interference between the first and second sets.

13. The tool of claim 10, wherein the second detector/source set is contained in a second body of the tool, and wherein the second body is connected to the first body via a connector, wherein the second detector/source set is spaced apart from the first detector/source set, wherein a photon insulating material is positioned in the connector of the second body, and wherein the insulating material and the first and second set spacing reduces interference between the first and second sets.

14. A method for evaluating an integrity of cement in a wellbore with multiple casing strings, the method comprising the operations of:
 adjusting a first radial depth of investigation (DOI) of a first detector/source set of a logging tool by adjusting a first distance between a first detector and a first source of the first detector/source set;
 positioning the logging tool in the wellbore;
 emitting a field of photons from the first source;
 radiating a first annulus outside a first casing string with photons from the first source, with at least a portion of the first source photons traveling into the first annulus and being scattered back to the first detector,
 detecting the scattered photons from multiple azimuthal directions around a circumference of the first detector;
 producing photon count rates based on energy levels of the scattered photons detected by the first detector; and
 determining an integrity of cement in the first annulus based on the first detector count rates;
 wherein the first detector is a non-azimuthally collimated photon detector.

15. The method of claim 14, wherein the determining further comprises comparing first detector count rates to expected count rates for the first annulus, and the comparing determines a presence of cement in the first annulus.

16. The method of claim 15, wherein the comparing determines a reduced integrity of the cement in the first annulus, and wherein the reduced integrity is selected from a group consisting of a void, a fracture, a fissure, a crack, an area of erosion, an area of degradation, and any combination thereof.

17. The method of claim 14, further comprising adjusting a second radial DOI of the first detector/source set by adjusting a second distance between a second detector and the first source of the first detector/source set.

18. The method of claim 17, further comprising:
 radiating a second annulus outside a second casing string with photons from the first source, with at least a portion of the first source photons traveling into the second annulus and being scattered back to the second detector,
 detecting the scattered photons from multiple azimuthal directions around a circumference of the second detector;

producing photon count rates based on energy levels of the scattered photons detected by the second detector; and determining an integrity of cement in the second annulus based on the second detector count rates.

19. The method of claim 18, further comprising adjusting a third radial DOI of a second detector/source set by adjusting a third distance between a third detector and a second source of the second detector/source set.

20. The method of claim 19, further comprising:

radiating a third annulus outside a third casing string with photons from the second source, with at least a portion of the second source photons traveling into the third annulus and being scattered back to the third detector, detecting the scattered photons from multiple azimuthal directions around a circumference of the third detector;

producing photon count rates based on energy levels of the scattered photons detected by the third detector; and determining an integrity of cement in the third annulus based on the third detector count rates; and connecting the first and second detector/source sets together via a connector to form the logging tool.

21. A system for evaluating integrity of cement in a wellbore with multiple casing strings, the system comprising:

a conveyance; and a logging tool that is run to various locations in the wellbore via the conveyance, the tool comprising:

a first body, a first photon source contained in the first body that produces a field of photons emitted from the first source, and a first photon detector contained in the first body and spaced away from the first photon source by a first distance that sets a first radial depth of investigation (DOI) of the first detector, with photon count rates produced by the first detector that are based on energy levels of scattered photons received by the first detector from materials surrounding the wellbore, wherein the first detector is a non-azimuthally collimated photon detector.

22. The tool of claim 21, wherein increasing the first distance increases the first radial DOI and decreasing the first distance decreases the first radial DOI.

23. The tool of claim 21, wherein the field of photons emitted from the first source is one of a substantially cone-shaped field and a panoramic field, and wherein the first radial DOI indicates a reduced integrity of cement in a first annulus.

* * * * *